(12) United States Patent
Severns

(10) Patent No.: US 7,614,746 B2
(45) Date of Patent: Nov. 10, 2009

(54) MACULAR FUNCTION TESTER

(75) Inventor: Matthew L. Severns, Kensington, MD (US)

(73) Assignee: LKC Technologies, Inc, Gaithersburg, MD (US)

( * ) Notice: Subject to any disclaimer, the term of this patent is extended or adjusted under 35 U.S.C. 154(b) by 0 days.

(21) Appl. No.: 11/980,071

(22) Filed: Oct. 27, 2007

(65) Prior Publication Data
US 2009/0109399 A1 Apr. 30, 2009

(51) Int. Cl.
A61B 3/10 (2006.01)
A61B 3/02 (2006.01)
A61B 3/00 (2006.01)
(52) U.S. Cl. ................. 351/221; 351/226; 351/246
(58) Field of Classification Search .......... 351/200–246
See application file for complete search history.

(56) References Cited

U.S. PATENT DOCUMENTS

| 3,664,732 A | | 5/1972 | Lynn | 351/246 |
|---|---|---|---|---|
| 4,784,483 A | * | 11/1988 | Holladay et al. | 351/243 |
| 5,459,536 A | | 10/1995 | Shalon et al. | 351/226 |
| 5,822,037 A | | 10/1998 | Barad | 351/224 |
| 6,086,204 A | * | 7/2000 | Magnante | 351/212 |
| 6,319,273 B1 | * | 11/2001 | Chen et al. | 607/88 |
| 6,578,965 B2 | | 6/2003 | Grant | 351/214 |
| 2003/0212310 A1 | | 11/2003 | Febbroriello et al. | 600/249 |
| 2004/0193070 A1 | | 9/2004 | Schilder et al. | 600/558 |
| 2006/0227290 A1 | | 10/2006 | Murray et al. | 351/243 |

OTHER PUBLICATIONS

Binns et al; Evaluation of Retinal Function using the Dynamic focal Cone, Ophthalmic Physiol. Opt. 2005; 25:492-500.
Binns, Alison et al; Development of a technique for recording the focal rod ERG; Ophthalmic Physiol. Opt. 2006; 26:71-79.
Krakau et al; A Computerised Adaptometer, Acta Ophthalmol Scan, 1998; 76:125-127.
Friedburg et al; A computer-controlled system for measuring dark adaptation etc., Graefe's Arch Clin Exp Ophthalmol. 1998; 236:31-40.
Owsley et al; Delays in Rod-mediated Dark Adaptation in Early Age-related Maculopathy; Ohthalmology, 2001; 108(7): 1196-1202.
Owsley et al; Psychophysical Evidence for Rod Vulnerability in Age-Related Macular Degeneration, Invest. Vis. Sci, 2000; 41(1): 267-73.

* cited by examiner

Primary Examiner—Mohammed Hasan
(74) Attorney, Agent, or Firm—Roger M. Rathbun

(57) ABSTRACT

A device to carry out tests of the macula of a subject's eye to identify disease such as age related macular degeneration. The device includes a stimulus light source comprising a stimulus spheroidal chamber with a stimulus light located therein to emit light through an aperture in the stimulus spheroidal chamber into the eye of a subject. The stimulus light source may include a plurality of light emitting diodes of differing colors. A controller controls the intensity and the color of the light emitted through the aperture of the stimulus spheroidal chamber to the subject. There is also an adapting light source comprising a light contained within an adapting spheroidal chamber. The adapting light source provides a bright light that can be used to remove the subject's dark adaption. There is also an alignment detection system that verifies that the gaze of the subject is toward the stimulus light source.

19 Claims, 2 Drawing Sheets

MACULAR FUNCTION TESTER

FIELD OF THE INVENTION

The present invention relates to a device for testing the macula of the eye of a human subject and, more particularly, to a device that can be used to carry out certain tests on that macula.

BACKGROUND OF THE INVENTION

Age related macular degeneration (often called AMD) is the leading cause of blindness in adults over the age of 50. AMD is a form of degeneration of the macula, which is the part of the retina responsible for the sharp central vision needed to read or drive.

Dry AMD is an early stage of the disease, and may result from the aging and thinning of macular tissues, depositing of pigment in the macula, or a combination of the two processes. Dry macular degeneration is currently diagnosed when yellowish spots known as drusen begin to accumulate from deposits of debris from deteriorating tissue primarily in the area of the macula. Gradual central vision loss may occur with dry macula degeneration but is not nearly as severe as symptoms associated with the wet form of AMD.

In about 10% of cases, dry AMD progresses to a more advanced and damaging form of the eye disease know as wet macular degeneration. With wet AMD, new blood vessels grow (neovascularization) beneath the retina and leak blood and fluid. The leakage causes permanent damage to light-sensitive retinal cells, which die off and create blind spots in central vision. Neovascularization, the underlying process causing wet AMD and abnormal blood vessel growth, is the body's misguided way of attempting to create a new network of blood vessels to supply more nutrients and oxygen to the eye's retina. But the process instead creates scaring leading to sometimes severe central vision loss.

New treatments are beginning to be available for the treatment of AMD, including photodynamic therapy where a photosensitizing drug is injected into the patient, which is then activated in the area of the AMD using a bright light such as a laser. Vascular Endothelial Growth Factor (VEGF) inhibitors have also been shown to treat this condition. In all cases, however, the treatments available today merely arrest further development of the disease and do not normally cause a reversal of the disease process. Thus, it is of interest to detect the occurrence of damaging forms of AMD early in the disease process so that treatment can begin as soon as possible to slow or arrest AMD progression and preserve visual function.

The current standard test for detection of AMD is the Amsler Grid. This is simply a grid of horizontal and vertical lines printed on a piece of paper. The subject observes the grid and notes if there are any places where the lines appear broken or wavy. This test is useful for detecting existing AMD, but there must already be significant visual deficits before the Amsler Grid shows abnormalities.

Another test currently in use is visual fields. In this test, spots of light are flashed in various locations in the field of vision and the brightness of the spots form a map that can be used to determine if there are losses of central vision. Another common test to detect AMD is the multifocal electroretinogram, which measures the electrical response of the retina to a flashing light. All of these tests work to some degree in detecting AMD but are either not very sensitive or are cumbersome to administer. In addition, these tests are only effective in detecting AMD once damage has already occurred.

There are a few easily-administered tests available for early detection of AMD. Owlsey and coworkers at the University of Alabama developed a test that measured the ability of the eye to detect dim flashes of light in the central 12 degrees of vision. This is very similar to the conventional visual field test, but the flashes of light are much dimmer and are presented after a bright light removes the subject's dark adaption, a process known as bleaching. Based upon published studies, this testing technique appears to sensitively detect early AMD.

Another recent test for detection of AMD involves presenting a flash of light to the central retina and measuring the electrical response of the macular rods; a form of electroretinogram. This test also appears to sensitively detect early AMD.

One of the common systems for dark adaptometry is the Goldman-Weekers adaptometer which produces a spot of light of adjustable intensity in an integrating sphere, however, that device uses filters to produce light of different colors and intensities and does not have an electronic control of the color and intensity of the adapting light. In addition, that adaptometer has no simple mechanism to monitor the direction of the gaze of the subject.

Another common adaptometer in current use is the SST-1 adaptometer of LKC Technologies, Inc. but the stimulus of that device is a ganzfeld (whole field) stimulus and does not present a focal stimulus. In addition, the SST-1 device uses only green light emitting diodes to present the stimulus and has no means of monitoring the direction of the gaze of the subject.

Accordingly, it would be advantageous to have a device that is capable of carrying out the testing of the macula of the eye of a subject easily and efficiently in order to obtain an early recognition of the presence of AMD in a subject at an early stage.

BRIEF SUMMARY OF THE INVENTION

Therefore, with the present invention, there is provided a device that can be used to carry out a number of tests of the macula of an eye of a subject easily and efficiently. With the present device, the following tests of the macula can be conducted, among others, as follows:

Test 1: determining the subject's threshold after adapting to the dark. This test is conducted without the use of an adapting light and, in the test, a light is turned on for a period of, typically 1-2 seconds and the subject responds. One way of determining the response can be by means of a pushbutton. The brightness of the light is adjusted on each trial until the subject's threshold is reached i.e. the subject sees the light 50% of the time.

Test 2: in this test, an adapting light is first presented to set the subject's light adaptation to a predetermined state. Then the process of Test 1 is repeated over time (frequently 30-45 minutes) to determine the time course of the threshold intensity.

Test 3: this test measures the electrical response of the eye to the stimulus using an electroretinogram as described in a paper by Binns, A. Margrain, TH, Development of a technique for recording the focal rod ERG, Opthalmic Physiol Opt. 2006, January: 26(1): 71-9.

As such, the macula testing device of the present invention can be used to carry out all of the above tests as well as many others that are currently used or which may be devised in the future. The present invention is in a device for testing the macula of a subject's eye and includes a stimulus light source that emits a light toward the subjects eye and is focused by the eye onto the macula. That stimulus light source comprises a plurality of lights located within the stimulus spheroidal chamber that has a stimulus aperture. The light from the plurality of lights is mixed by the interior surface of the stimulus spheroidal chamber and is emitted through the stimulus aperture to be directed toward the subject's eye. The invention also includes a controller that controls the intensity as well as the color output of the lights so as to control the light that is directed toward the eye of the subject via the stimulus aperture.

As a further feature of the present invention, the plurality of lights can be of different colors and can be light emitting diodes. The controller can, therefore, select lights of certain colors and can vary the duty cycles of one or more light to control the intensities.

Another feature of the present invention is in an adapting light that can be used to direct a bright light toward the eye of the subject. The adapting light can be positioned within an adapting spheroidal chamber having an adapting aperture such that the light is again mixed by the internal surface of the spheroidal chamber and emitted through the adapting aperture toward the eye of a subject as a even, uniform light.

In an exemplary embodiment, the adapting light may pass along the same path as the stimulus light with the adapting aperture aligned with the stimulus aperture such that the light emitted from the stimulus aperture passes through the adapting spheroidal chamber to pass out of the adapting aperture toward the eye of the subject.

The present invention can also include an alignment detection system that can be used to assure that the stimulus aperture is in proper alignment to direct light toward the eye of the subject. The alignment detection system can include an alignment light that is directed toward the eye of the subject and a detector, which can be a camera, that receives light reflected from the eye. When the stimulus aperture is in the correct alignment for light to pass therefrom into the eye of the subject, that is, the subject is looking straight at the stimulus aperture, the light from the alignment light will flood the pupil and be detected by the camera. Thus, with the use of the alignment detection system, the user can be assured that the gaze of the subject is directed toward the stimulus aperture.

As can therefore be seen, the present macula testing device can provide both a colored or white stimuli to the central, or macular, part of the eye for the purpose of carrying out the aforedescribed tests, or other tests, in order to detect various eye diseases including AMD. If the stimulator is used for dark adaptometry, the whole eye can first be subjected to a bright adapting light which brings the eye to a state where the visual pigments of the eye are largely depleted. With the present device, the bright adapting light can be provided by a bright light located within a separate adapting spheroidal chamber to provide an even light or, alternatively, the adapting light can be provided by a bright light located within the stimulus spheroidal chamber. Following the bright light, the present device can then provide a stimulus light directed to the central 5 to 10 percent of the eye's visual field and can be adjusted in intensity and/or color to carry out the testing of the macula of the eye. Thus, the present macula testing device can provide two different, controllable, light sources, one for adapting and one for stimulus, in order to carry out various tests of the macula of the eye of a subject.

These and other features and advantages of the present invention will become more readily apparent during the following detailed description taken in conjunction with the drawings herein.

DETAILED DESCRIPTION OF THE INVENTION

Figure 1:
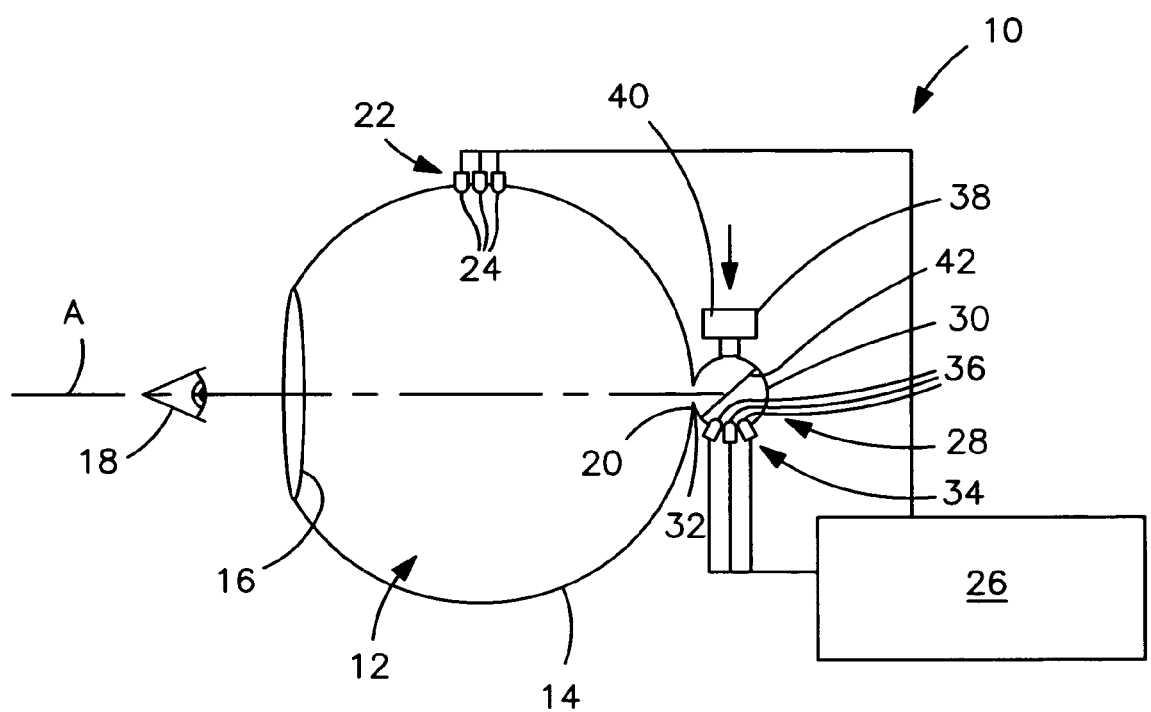
FIG. 1 is a schematic view of the macular testing device constructed in accordance with the present invention.
Figure 2:
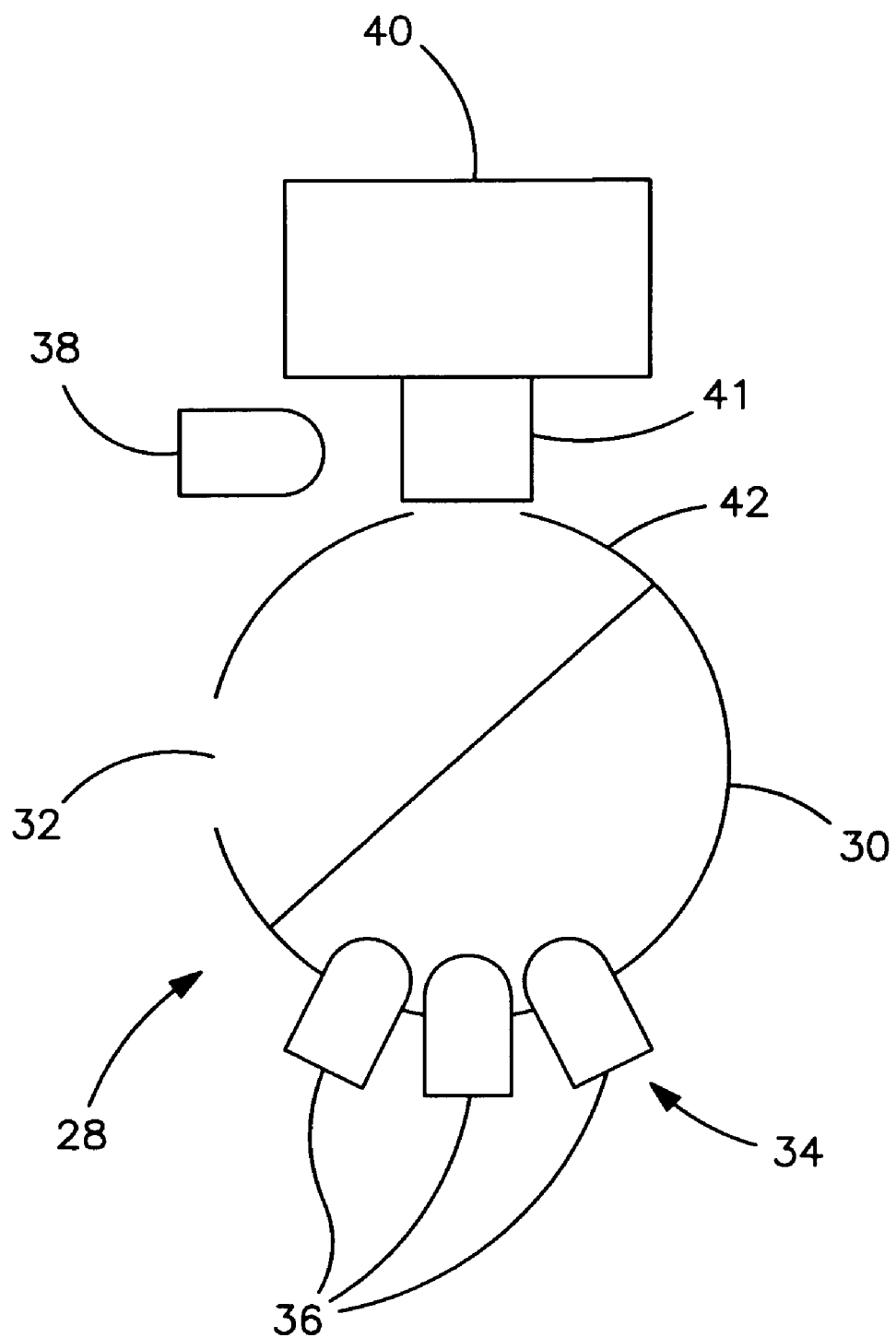
FIG. 2 is an enlarged schematic view of the device of FIG. 1.

Referring now to FIGS. 1 and 2, there is shown a schematic view of the present macular testing device 10 and an enlarged schematic view of a certain components of the device of FIG. 1, respectively. As can be seen, the macular testing device 10 includes an adapting light source 12 comprised of an adapting spheroidal chamber 14 having a first aperture 16 that is located generally in alignment with the eye 18 of a subject and a second aperture 20 that is positioned about opposite of the first aperture 16. The diameter and positioning of the second aperture 20 may vary, however, in the exemplary embodiment, it is adapted to emit light, as will be seen, at an angle of between about 5 degrees and 10 degrees into the eye 18 of the subject.

There is an adapting light 22 that emits light within the interior of the adapting spheroidal chamber 14 and the adapting light 22 may be a single light, such as an incandescent bulb, or may be comprised of a plurality of light emitting diodes 24 and the intensity of the light emitted by the adapting light 22 can be controlled by a controller 26 by varying the power or by adjusting the duty cycles of the light emitting diodes 24.

As can thus far be seen, the light emitted by the adapting light 22 is reflected off of the interior surface of the adapting spheroidal chamber 14 to emit an even, constant light through the first aperture 16 and into the eye 18 of the subject. The intensity of the emitted light is controlled by the user or by some other control scheme by means of the controller 26. As previously stated, the purpose of the adapting light source 12 is to provide a high intensity light into the eye 18 of the subject in order to bring the eye to a state where the rhodopsin in the eye is largely depleted and that step is generally followed by a further step in the testing of the macula of the subject's eye.

That further step in the testing is normally carried out by the use of the stimulus light source 28. The stimulus light source 28 comprises a stimulus spheroidal chamber 30 having an aperture 32 that is also located generally in alignment with the eye 18 of a subject. By alignment, it is meant that the aperture 32 of the stimulus spheroidal chamber 30 is generally aligned along a path A and the first and second apertures 16, 20 are also aligned along that path and which aligns with the eye 18 of the subject.

A stimulus light source 34 is provided within the stimulus spheroidal chamber 30 and may comprise a plurality of individual stimulus lights 36 such as light emitting diodes. In the exemplary embodiment, these can be a plurality of colored lights. The stimulus light source 34 is out of the line of sight of the subject's eye 18, that is, it is displaced away from the path A. Again the controller 26 controls the intensity of the stimulus lights 36 and also can individually control the selection of the colored light or lights so that the controller 36 can control both the intensity and the color of the light that is reflected around the interior surface of the stimulus spheroidal chamber 30 and out through the aperture 32 uniform in brightness and color. As can be seen, the stimulus light passes along the path A to the eye 18 of a subject by passing through both the first and second apertures 16, 20 of the adapting spheroidal chamber 14.

The brightness of the stimulus light source 34 can be adjusted by using pulse width modulation or other techniques to achieve the desired intensity and color. The brightness of the stimulus lights 36 can be varied over a range of at least 30000 to 1 (4.5 log units of intensity) using pulse width modulation. Greater brightness range can be accomplished by using more that one set of light emitting diodes and restricting the output of the second set though a filter or aperture. The light emitting diodes can also be controlled to produce stimuli other than a constant light, for example, flickering light either on-off or between two colors or luminances.

There is also an alignment detection system that verifies that the path A is in alignment with the eye 18 of the subject, that is, the light emitted from the second aperture 20 of the stimulus spheroidal chamber 30 is aiming that light directly toward the eye 18. Taken in reverse, the alignment detection system assures that the eye 18 of the subject is directed along the path A. The alignment system includes a light source 38 having a wavelength generally in the near infrared spectrum (about 880 nm to about 910 nm region) and a light detector 40, such as a camera, that is sensitive to light in that portion of the spectrum.

The light from the light source 38 thus passes through the collimating lens and beamsplitter 31, is reflected by the beam splitter 42 to pass through the aperture 32 and 16 to reach and reflect off of the eye 18 of the subject. The reflected light returns through the aperture 32 to be received by the light detector 40 again after reflection by the beamsplitter 42. The use of the collimating lens and beamsplitter 41 and the beamsplitter 42 allows the light source 38 and light detector 40 to be displaced away from the path A or out of the line of vision of the subject's eye 18. The collimating lens and beam splitter 31 both collimates the light from the light source 38 as well as focuses the image of the eye 18 onto the light detector 40.

Accordingly, in the use of the alignment detection system, the near-infrared light from the light source 38 enters the eye 18 and when the gaze of the eye 18 is directed towards the aperture 32, the pupil of the eye 18 will appear to flood with light and which can be detected by the light detector 40. As such, the operator can determine, or a computer-programmed process can carry out the steps, and verify that the subject is looking directly toward the aperture 32.

Those skilled in the art will readily recognize numerous adaptations and modifications which can be made to the of the present invention which will result in an improved device and method of using the same, yet all of which will fall within the scope and spirit of the present invention as defined in the following claims. Accordingly, the invention is to be limited only by the following claims and their equivalents.

What is claimed is:

1. A device for testing the macula of the eye of a human subject, the device comprising a stimulus light source for emitting a light to be directed toward the macula of an eye of a human subject, the stimulus light source comprising at least one light located within a stimulus spheroidal chamber having a stimulus aperture and the at least one light is mixed by the interior surface of the stimulus spheroidal chamber and emitted through the stimulus aperture toward an eye of a subject, a second chamber affixed to the stimulus spheroidal chamber, said second chamber having a first aperture adapted to be positioned proximate to the eye of a subject and a second aperture opposite thereto, said second chamber being aligned with the stimulus light chamber such that light emitted by the at least one light passes through the stimulus aperture and both the first and second apertures of the second chamber toward the eye of a patient, and an electronic controller to control the intensity and the color output from the at least one light.

2. The device of claim 1 wherein the at least one light comprises a plurality of lights of at least two different colors.

3. The device of claim 2 wherein the plurality of lights are light emitting diodes.

4. The device of claim 1 wherein the controller varies the duty cycle of the at least one light.

5. The device of claim 1 wherein the device further includes an adapting light positioned within the second chamber for directing a bright light toward the eye of a human subject.

6. The device of claim 5 wherein the second chamber is spheroidal.

7. The device of claim 6 wherein the device includes a microprocessor that controls the intensity of the adapting light.

8. The device of claim 7 wherein the adapting light comprises at least one light emitting diode.

9. The device of claim 1 wherein the device includes an alignment detection system that determines when a pupil of a subject is directed towards the stimulus aperture.

10. The device of claim 9 wherein the alignment detection system comprises an alignment light directed toward an eye of a subject and a camera to receive reflected alignment light from an eye of a subject to determine when a pupil of a subject is directed towards the stimulus aperture.

11. The device of claim 10 wherein the alignment light directed toward the eye of a subject and the reflected light received by the camera passes through the stimulus aperture.

12. The device of claim 11 wherein the device includes a beamsplitter located within the stimulus spheroidal chamber that directs the reflected light passing through the stimulus aperture to a camera located to one side of the stimulus aperture.

13. The device of claim 10 wherein the alignment light emits light in the near-infrared spectrum.

14. A system for detecting the condition of the macula of an eye of a subject comprising:

a device having a first spheroidal chamber and a second spheroidal chamber, the first spheroidal chamber having a first aperture adapted to be positioned proximate to the eye of a subject and a second aperture opposite thereto, the second spheroidal chamber having a aperture generally in alignment with the second aperture of the first spheroidal chamber an adapting light source located within the first spheroidal chamber and adapted to be illuminated to produce a light that passes through the first aperture toward the eye of a patient, an adapting controller that controls the intensity of the adapting light source, a stimulus light source located within the second spheroidal chamber and having a plurality of color lights of differing colors, a stimulus controller that controls the selection of color lights and intensity thereof to produce a stimulus light of a desired color and intensity to pass through the aperture of the second spheroidal chamber and through the second and first apertures of the first spheroidal chamber toward the eye of a subject.

15. The system as defined in claim 14 wherein the system further includes an alignment system to align the first and second apertures of the first spheroidal chamber and the aperture of the second spheroidal chamber with the eye of a subject.

16. The system as defined in claim 15 wherein the alignment system comprises a source of near-infrared light directed toward the eye of a subject and a receiver to receive the near-infrared light reflected from the eye of a subject.

17. The system as defined in claim 16 wherein the infrared light is directed along a line passing through the first and second apertures of the first spheroidal chamber and the second aperture of the second spheroidal chamber.

18. The system as defined un claim 17 wherein the receiver is a camera.

19. The system as defined in claim 17 wherein the near-infrared light is directed along the line by means of a beamsplitter and wherein the near-infrared light source and camera are located off of the line.

* * * * *